United States Patent
Rogers

(10) Patent No.: US 11,224,492 B1
(45) Date of Patent: Jan. 18, 2022

(54) SURGICAL DRAPE AND METHOD

(71) Applicant: Tosha L. Rogers, Fairburn, GA (US)

(72) Inventor: Tosha L. Rogers, Fairburn, GA (US)

(*) Notice: Subject to any disclaimer, the term of this patent is extended or adjusted under 35 U.S.C. 154(b) by 965 days.

(21) Appl. No.: 15/266,616

(22) Filed: Sep. 15, 2016

Related U.S. Application Data

(60) Provisional application No. 62/218,777, filed on Sep. 15, 2015.

(51) Int. Cl.
A61B 46/00 (2016.01)
A61B 46/20 (2016.01)

(52) U.S. Cl.
CPC .............. *A61B 46/30* (2016.02); *A61B 46/20* (2016.02); *A61B 46/40* (2016.02); *A61B 2046/201* (2016.02); *A61B 2046/205* (2016.02)

(58) Field of Classification Search
CPC ......... A61B 46/00; A61B 46/10; A61B 46/20; A61B 46/23; A61B 46/30; A61B 46/40; A61B 2046/201; A61B 2046/205; A61B 2046/234; A61B 2046/236
USPC .......................... 123/849; 128/849, 852, 853
See application file for complete search history.

(56) References Cited

U.S. PATENT DOCUMENTS

| | | | |
|---|---|---|---|
| 3,677,266 A | 7/1972 | Green | |
| 3,800,790 A | 4/1974 | Collins | |
| 4,520,807 A * | 6/1985 | Rotter | A61B 17/42 128/849 |
| 2010/0139669 A1 * | 6/2010 | Piferi | A61B 46/23 128/852 |
| 2010/0300459 A1 * | 12/2010 | Lair | A61B 50/30 128/853 |
| 2012/0222686 A1 * | 9/2012 | Lockwood | A61M 1/0088 128/849 |
| 2013/0104908 A1 * | 5/2013 | Lager | A61B 46/00 128/851 |
| 2013/0261419 A1 * | 10/2013 | Davidson | A61B 10/007 600/365 |
| 2014/0116448 A1 * | 5/2014 | Mackovic-Basic | A61F 5/451 128/849 |

* cited by examiner

*Primary Examiner* — Alireza Nia
*Assistant Examiner* — Daniel A Miller
(74) *Attorney, Agent, or Firm* — Schwartz Law Firm, P.C.

(57) ABSTRACT

A surgical drape is adapted for use by a woman during childbirth. The surgical drape includes a fecal collection panel having top, bottom, and opposing side edges. An adhesive is applied to a top marginal area of the collection panel directly adjacent its top edge. The adhesive is adapted for temporarily holding the top edge of the collection panel below the vagina and above the anus of the woman when disposed in a lithotomy position, while the bottom edge of the collection panel resides beneath the buttocks. The collection panel defines a protected access aperture designed for enabling ready access by a delivery assistant to the anus of the woman during childbirth. The protected aperture comprises a line of perforations extending perpendicular from the top marginal area of the collection panel towards the bottom edge.

8 Claims, 3 Drawing Sheets

SURGICAL DRAPE AND METHOD

TECHNICAL FIELD AND BACKGROUND OF THE DISCLOSURE

The present disclosure relates broadly and generally to a disposable surgical drape and method. In one exemplary application, the present surgical drape may be used in hospitals during labor and delivery. Childbirth can be an intense and emotional time for the mother-to-be as she moves through the various stages of labor and delivery. The last thing any woman wants to think about is the possibility of having a bowel movement while giving birth. Although it is a very common occurrence, it is also a source of shame and embarrassment for many women during the birthing process.

The present drape of the exemplary disclosure is a solution for doctors and patients hoping to avoid this type of embarrassment. Essentially, the exemplary drape is designed to separate the vaginal area from the anus thereby reducing the visibility and smell of any fecal waste leaving the body during delivery. This method allows doctors to maintain a sterile work environment while putting the patient's mind at ease about the possibility of having a bowel movement during delivery or transmitting a disease to the unborn child.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a surgical drape adapted for use by a woman during childbirth. The exemplary surgical drape comprises a fecal collection panel having top, bottom, and opposing side edges. An adhesive is applied to a top marginal area of the collection panel directly adjacent its top edge. The adhesive is adapted for temporarily holding the top edge of the collection panel below the vagina and above the anus of the woman when disposed in a lithotomy position, while the bottom edge of the collection panel resides beneath the buttocks. The collection panel defines a protected access aperture designed for enabling ready access by a delivery assistant (e.g., physician, nurse, midwife, or the like) to the anus of the woman during childbirth. The protected aperture comprises a line of perforations extending perpendicular from the top marginal area of the collection panel towards the bottom edge.

According to another exemplary embodiment, the top marginal area of adhesive has a width dimension designed to span a distance no greater than an anogenital distance between the anus and the vagina.

According to another exemplary embodiment, the top marginal area of adhesive is designed to cover a perineum of the woman.

According to another exemplary embodiment, the line of perforations extends into the top marginal area of adhesive and begins just below the top edge of the collection panel.

According to another exemplary embodiment, the line of perforations is between 1 and 3 inches in length.

According to another exemplary embodiment, the collection panel comprises a polyethylene film.

According to another exemplary embodiment, the adhesive is latex-free and hypoallergenic.

According to another exemplary embodiment, a disposable release paper (e.g., silicone release paper) is adapted for temporarily covering the marginal area of adhesive.

According to another exemplary embodiment, the marginal area of adhesive extends substantially continuously from one side edge of the collection panel to the other.

In another exemplary embodiment, the present disclosure comprises a method of utilizing a surgical drape applied to a woman during childbirth. The surgical drape comprising a fecal collection panel and protected access aperture. The method includes locating a bottom edge of the fecal collection panel beneath the buttocks of the woman. Fecal waste excreted by the woman (during labor) is then captured on the fecal collection panel. Prior to delivering the child, a top edge of the fecal collection panel (with captured fecal waste) is lifted to extend between the vagina and anus of the woman. The top edge of the fecal collection panel is temporarily adhered to the legs of the woman. The anus of the woman can then be accessed through the protected aperture formed with the fecal collection panel.

According to another exemplary embodiment, the method comprises, after delivering the child, removing and discarding the fecal collection panel.

According to another exemplary embodiment, wherein accessing the anus of the woman through the protected aperture comprises bursting a line of perforations formed with the fecal collection panel.

BRIEF DESCRIPTION, OF THE DRAWINGS

Exemplary embodiments of the present disclosure will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
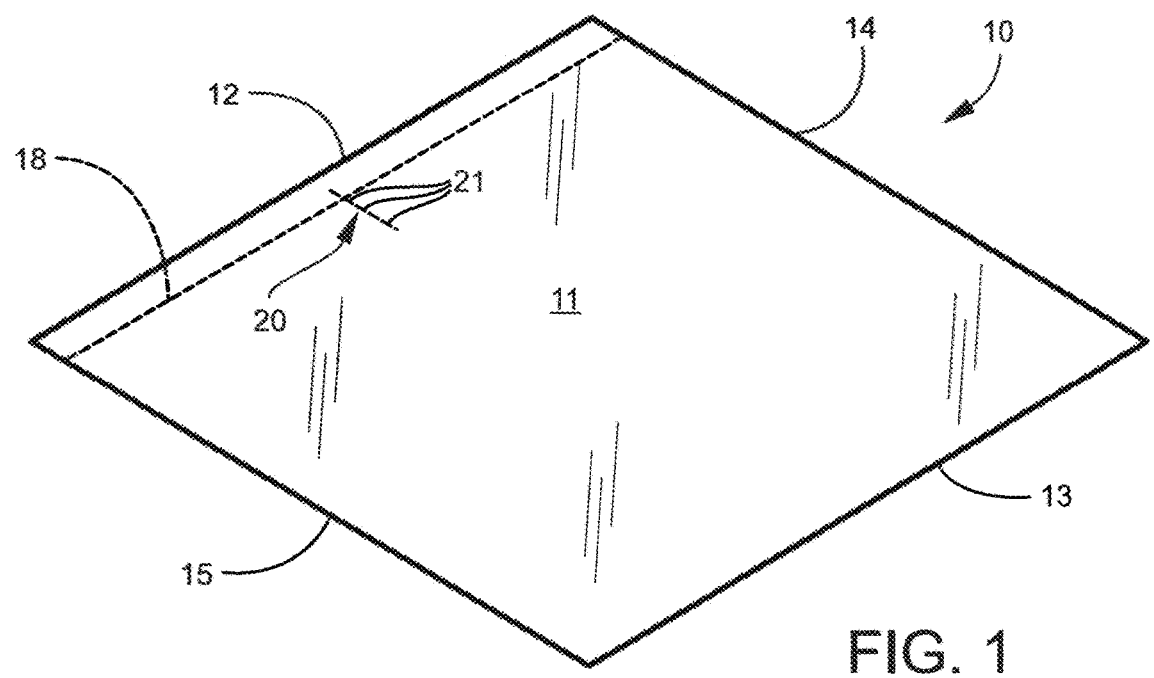
FIG. 1 is a first perspective view showing an outside surface of the exemplary surgical drape laid flat.
Figure 2:
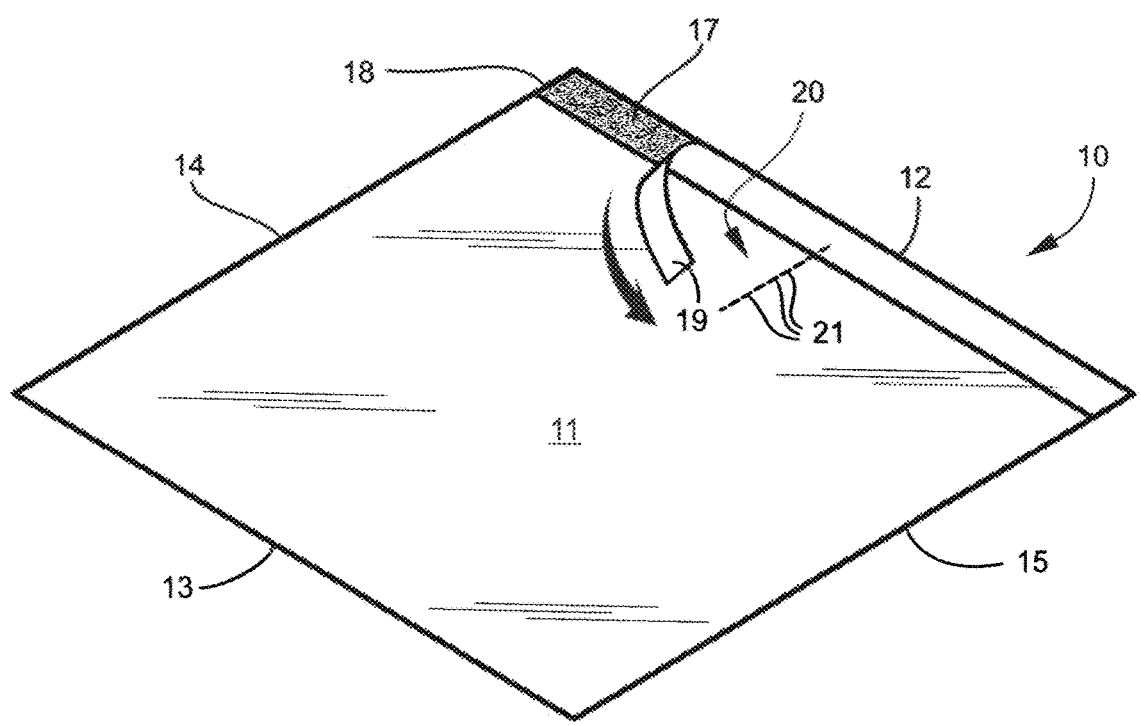
FIG. 2 is a second perspective view showing an inside surface of the exemplary surgical drape laid flat, and illustrating the process of peeling away release paper to expose contact adhesive applied to a top marginal area of the fecal collection panel.

Referring now specifically to the drawings, a disposable surgical drape according to one exemplary embodiment of the present disclosure is illustrated in FIGS. 1 and 2, and shown generally at broad reference numeral 10. The exemplary surgical drape 10 is particularly applicable for use by women during childbirth, and functions to help maintain a clean and sterile delivery area throughout the delivery process. The surgical drape 10 may also alleviate any shame or embarrassment experienced by women after defecating during the pushing phase of labor.

As shown in FIGS. 1 and 2, the exemplary surgical drape 10 comprises a fecal collection panel 11 having top 12, bottom 13, and opposing side edges 14 and 15. The collection panel 11 may be fabricated of any suitable continuous-surface (e.g., fluid impervious) material, such as polyethylene film, polypropylene, SMS fabric or the like. A medical grade contact adhesive 17 is applied to a top marginal area 18 of the collection panel 11 directly adjacent its top edge 12, and extends substantially continuously from one side edge 14 to the other 15. The marginal area 18 of adhesive has an approximate continuous width dimension of 1.0 inches, and functions as described further below to temporarily hold the top edge 12 of the collection panel 11 immediately below the vagina and above the anus of the woman when disposed in a lithotomy position, while the bottom edge 13 of the collection panel 11 resides beneath the buttocks. In one exemplary embodiment, the width of the adhesive marginal area 18 is designed to cover the woman's perineum, while spanning a distance no greater than an anogenital distance between the anus and the vagina. The exemplary adhesive 17 adheres well to the skin, and is latex-free and hypoallergenic to avoid irritation. As shown in FIG. 2, the adhesive 17 is temporarily covered by a peel-away silicone release paper 19 which may be removed by the physician (or other delivery assistant) immediately prior to use.

The exemplary collection panel 11 features a protected aperture 20 designed for enabling ready access by the physician to the anus of the woman during childbirth. The protected aperture 20 comprises a series of perforations 21 formed in a line substantially perpendicular to the top edge 12 of the collection panel 11, and beginning at a point within the marginal area 18 of adhesive and extending towards the bottom edge 13 of the collection panel 11. The length of the protected aperture 20 is between about 1 and 3 inches. To open the aperture 20, the physician simply separates the perforations 21 (e.g., by cutting or tearing) and pulls apart the opposing sides defining the access.

Figure 3:
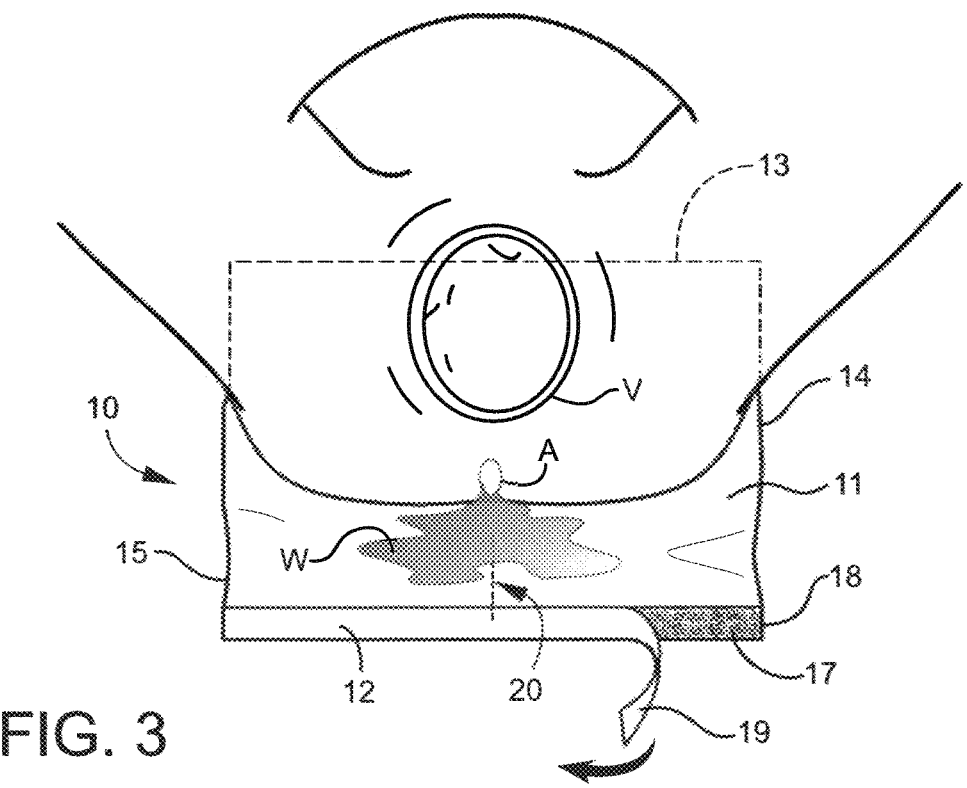
FIGS. 3, 4 and 5 demonstrate sequential application and use of the exemplary surgical drape.
Figure 4:
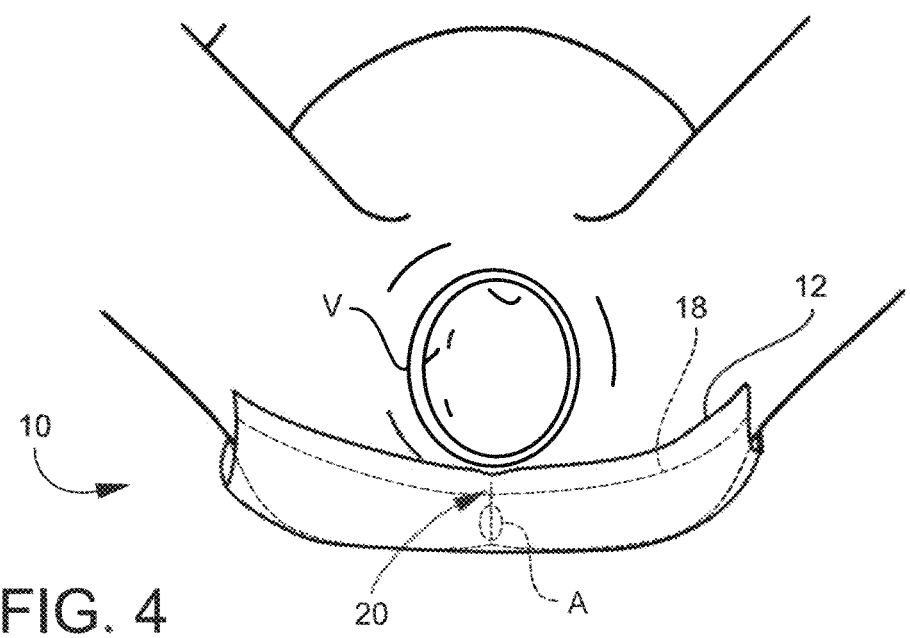
Figure 5:
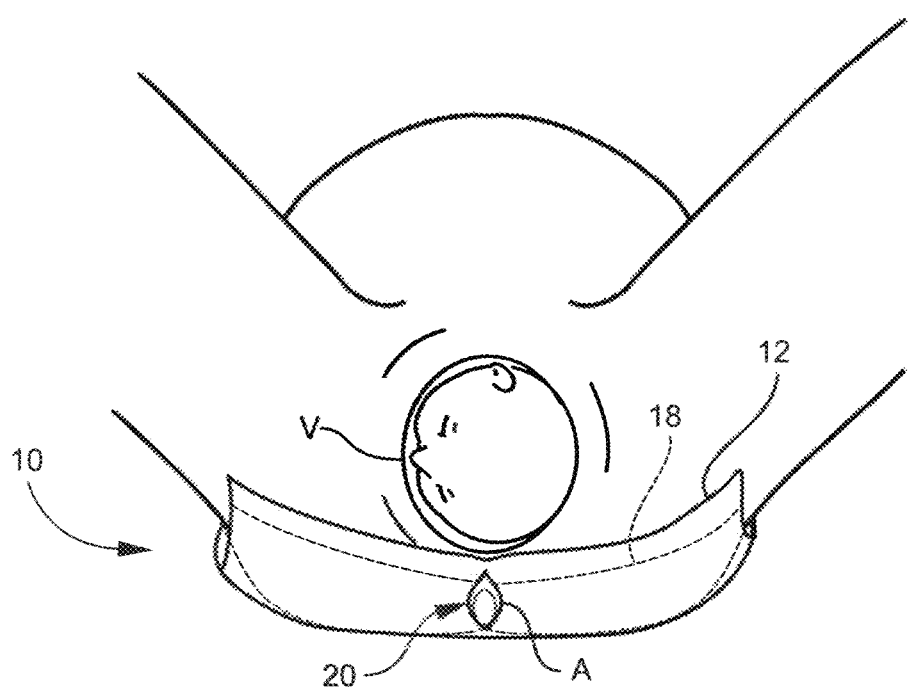

FIGS. 3, 4, and 5 demonstrate one exemplary application of the present surgical drape 10. As shown in FIG. 3, the bottom edge 13 of the fecal collection panel 11 is first positioned beneath the buttocks of the woman in the lithotomy position. As the woman bears down during the pushing phase of delivery, any excreted fecal waste "W" is captured on the collection panel 11. After the woman empties her bowels and prior to delivering the child, the release paper 19 is removed from the marginal area 18 to expose the adhesive 17 and the top edge 12 of the collection panel 11 (with captured fecal waste) is lifted and adhered directly to the legs and buttocks, as shown in FIG. 4. When properly applied, the marginal adhesive area 18 of the collection panel 11 extends between the vagina "V" and anus "A" of the woman. The surgical drape 10 thereby contains and substantially isolates the fecal waste from the vagina "V", and from the physician and other delivery assistants, during the remainder of the childbirth process. As shown in FIG. 5, if necessary the anus "A" of the woman can be accessed through the protected aperture 20 formed with the fecal collection panel 11 by separating the perforations 21 as described above. After delivering the child, the surgical drape 10 is removed from the woman and discarded. Alternatively, the top marginal area 18 of the collection panel 11 may be lifted and adhered to the woman as shown in FIG. 4 prior to any bowel movement, and may be removed from the woman immediately thereafter and discarded.

In one exemplary embodiment, the surgical drape 10 is substantially square (e.g., 22 inches×22 inches) and the protected access aperture 20 is approximately 2 inches in length. In alternative applications, the surgical drape 10 may be used in other childbirth positions including a side-lying birth position and various upright birth positions, such as squatting, standing, kneeling and all fours. The exemplary surgical drape 10 may offer AAMI Level 3 and AAMI Level 4 protection, and is sufficiently strong and impervious to fluids to effectively control and contain fluid and prevent strike-through.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed is:

1. A surgical drape adapted for use by a woman during childbirth, the woman having a vagina, an anus, and buttocks, said surgical drape comprising:

a fecal collection panel having top, bottom, and opposing side edges;

an adhesive applied to a top marginal area of said collection panel directly adjacent the top edge, said adhesive adapted for temporarily holding the top edge of said collection panel below the vagina and above the anus of the woman when disposed in a lithotomy position, while the bottom edge of said collection panel resides beneath the buttocks; and said collection panel defining a protected access aperture designed for enabling ready access by a delivery assistant to the anus of the woman during childbirth, said protected aperture comprising a line of perforations beginning at a point spaced from the top edge of said collection panel and within the top marginal area comprising said adhesive, and said line of perforations extending perpendicular from the top marginal area of said collection panel towards the bottom edge.

2. The surgical drape according to claim 1, wherein the top marginal area of said collection panel has a width dimension designed to span a distance no greater than an anogenital distance between the anus and the vagina.

3. The surgical drape according to claim 1, wherein the top marginal area of said collection panel is designed to cover a perineum of the woman.

4. The surgical drape according to claim 1, wherein the line of perforations is between 1 and 3 inches in length.

5. The surgical drape according to claim 1, wherein said collection panel comprises a polyethylene film.

6. The surgical drape according to claim 1, wherein said adhesive is latex-free and hypoallergenic.

7. The surgical drape according to claim 1, and comprising a disposable release paper adapted for temporarily covering the marginal area of said collection panel.

8. The surgical drape according to claim 1, wherein the marginal area of said collection panel extends substantially continuously from one side edge of said collection panel to an opposite side of said collection panel.

* * * * *